United States Patent

Nakayama et al.

[11] Patent Number: 5,825,182
[45] Date of Patent: Oct. 20, 1998

[54] NONDESTRUCTIVE TESTING SYSTEM USING A SQUID

[75] Inventors: Satoshi Nakayama; Kazuo Chinone; Akikazu Odawara; Tatsuaki Ataka, all of Chiba, Japan

[73] Assignee: Seiko Instruments Inc., Japan

[21] Appl. No.: 325,813

[22] Filed: Oct. 19, 1994

[30] Foreign Application Priority Data

Oct. 20, 1993 [JP] Japan .................................. 5-262741

[51] Int. Cl.⁶ ...................... G01N 27/87; G01R 33/035
[52] U.S. Cl. ............................................. 324/241; 324/225
[58] Field of Search ................................ 324/248, 238, 324/293, 240, 241, 242, 243, 225, 235, 262, 239

[56] References Cited

U.S. PATENT DOCUMENTS

| | | | |
|---|---|---|---|
| 3,422,346 | 1/1969 | Hammer | 324/241 |
| 3,611,120 | 10/1971 | Forster | 324/241 |
| 4,639,674 | 1/1987 | Rippingale | 324/326 |
| 5,289,121 | 2/1994 | Kajola et al. | 324/248 |
| 5,293,119 | 3/1994 | Podney | 324/248 |
| 5,331,278 | 7/1994 | Evanson et al. | 324/248 |

FOREIGN PATENT DOCUMENTS 0433482  6/1991  European Pat. Off. ............... 324/248

Primary Examiner—Walter E. Snow
Attorney, Agent, or Firm—Adams & Wilks

[57] ABSTRACT

In order to enhance the sensitivity of a nondestructive testing system, a pair of superconducting coils are disposed in the same plane such that a current flowing through the respective coils when exposed to a uniform magnetic field cancels out. As a result of this configuration, the detection coils are immune to noise, offset fields or other uniform ambient phenomena. In one embodiment, the nondestructive testing unit includes a plurality of detection coils, a SQUID having a pair of connectors for connection to the detection coils, a probe for supporting the detection coils and the SQUID in a coolant, a cryostat for supporting the probe and for keeping the coolant constant, a controller for processing a signal transmitted from the SQUID, and a display device for displaying the result of the processing. At least two detection coils are disposed in the same plane, are directly connected to the SQUID and are integrated on a semiconductor substrate.

16 Claims, 4 Drawing Sheets

NONDESTRUCTIVE TESTING SYSTEM USING A SQUID

BACKGROUND OF THE INVENTION

The present invention relates to a nondestructive testing system using a superconducting quantum interference device (SQUID) to be applied to high-sensitivity magnetic sensors.

As described in the Patent JP 1-245149, conventional nondestructive testing systems using a SQUID have been composed of a magnet meter and detection coils, in which a detection coil detects the magnetic field in the direction that is vertical to the SQUID and the sample, and the detection coils are, such as first- or higher-order vertical direction derivative coils. FIG. 2 shows the configuration of the nondestructive testing system using first-order bobbin-type derivative coils. As shown in FIG. 2, SQUID 4 comprises a superconductive closed circuit u1 having two Josephson junctions 42, 43, an input coil 44, a feedback coil 45, each of which are connected thereto, and a detection coil 5 which detects the magnetic field that is vertical to the coil surface is connected to said input coil 44.

Conventional nondestructive testing systems have had severe drawbacks in that background noise, possibly generated by a difference in level or a failure in uniformity or a problem with the state of the weld on the edge or surface of the sample, is significantly large and has caused problems in the detection of any small, weak signal given off by defects or scratches.

Furthermore, when measurement is made by applying an electric field and a magnetic field to the sample, offset noise is given off by the resulting magnetic field of the applied electrical field and the applied magnetic field. This noise has been known to bury the small, weak signal given off by micro-defects or scratches.

SUMMARY OF THE INVENTION

The object of the present invention is to offer a simple configuration, high-sensitivity nondestructive testing system which reduces background noise and/or offset noise generated by the applied magnetic field or by the surface and shape of the sample.

In conventional nondestructive testing systems, spatial resolution has been improved by minimizing the diameter of the detection coil, conventional sensitivity has been assured by increasing the number of turns, and the efficiency of magnetic flux transmission from said detection coils to the SQUID has been maximized by equalizing the inductance of the detection coil and the SQUID's input inductance. This provides conventional nondestructive testing systems with high sensitivity characteristics. However, the (equivalent) area, wherein the magnetic flux intersects, increases in proportion to the number of turns, but the inductance of the detection coil increases in proportion to the square of the number of turns. Thus, the inductance of the detection coil is restricted to the value of the SQUID's input inductance. In fact, detection coils ranging from one millimeter to several tens of millimeters have been used. To accurately detect scratches or defects in a submillimeter order, detection coils of a submillimeter order have been found to be required. The purpose of the present invention is to offer a nondestructive testing system which is capable of detecting small, weak defects, scratches, or deterioration, identifying and detecting adjacent defects which have not so far been detected, with highly-improved spatial resolution.

In order to solve the problems described above, the present invention is configured in such a way that two or more detection coils are aligned on the plane, wherein the base line which connects the center of each detection coil is parallel to the surface or the axis of the sample, and connected so that the direction of the current generated when said detection coils are positioned in the uniform magnetic field is negated. Said coils detect only the change on the plane that is vertical to the magnetic field.

In order to solve the above problems, the present invention is also configured in such a way that said detection coils are directly connected to the SQUID and both are integrated on a semiconductor substrate. Because the nondestructive testing system configured above detects only the differential amount (strength) of the magnetic flux which intersects two or more detection coils or loops, the magnetic flux which intersects two or more coils or loops becomes nearly equal. Consequently, said nondestructive testing system can eliminate noise, such as offset noise. Said device can also effectively attenuate (damp) background noise and other noise, whose differential amount is small and whose variation is slow.

Integrating said detection coils and the SQUID increases the spatial resolution without reducing the transmission efficiency of the magnetic flux, and micro scratches or defects can be detected with high accuracy.

DETAILED DESCRIPTION OF THE PREFERRED EMBODIMENTS

Embodiments of the present invention in accordance with drawings are explained below.

Figure 1:
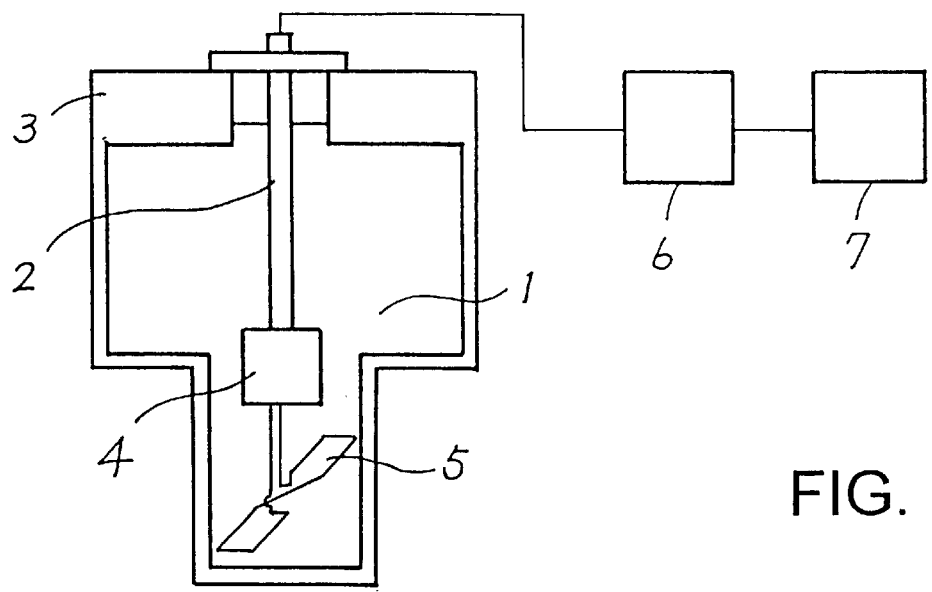
FIG. 1 shows a configuration of the nondestructive testing system of the invention.

FIG. 1 shows an embodiment of the present invention comprising coolant 1 which creates a superconductive status, cryostat 3 which maintains coolant 1 and supports a probe 2, SQUID 4 as well as detection coil 5, each of which are attached to said probe, a driver 6 which is electrically connected to SQUID 4, drives SQUID 4 and measures signal output, and a signal processor 7 which analyzes and displays said output signal.

Figure 3:
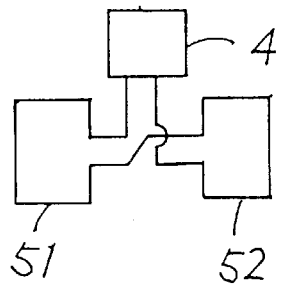
FIG. 3 is an explanation chart of the detection coil for the nondestructive testing system of the invention.

FIG. 3 shows an embodiment wherein two detection coils of equal area are attached, 51 and 52. The two detection coils are aligned on the same plane with one end of the first detection coil 51 connected to one end of the second detection coil 52, and the other end of both detection coils are each attached to a connector on SQUID 4. The direction of the current generated when the first detection coil 51 and the second detection coil 52 are positioned inside the uniform magnetic field is negated by SQUID 4. In this type of configuration, when each value of the magnetic field, which intersects each detection coil is the same, the current is offset, nothing is generated, and thus no signal is detected. However, when the value of the magnetic field differs, a current is generated in proportion to the differential of the magnetic field intersecting the coils. Said current is transmitted to SQUID 4, and becomes a detection signal corresponding to the differential of the magnetic field, and it is output to the processor.

Figure 4:
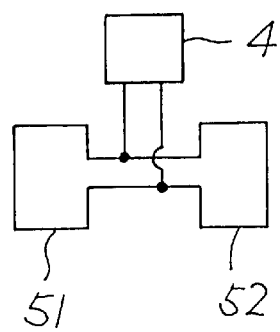
FIG. 4 is an explanation chart of the detection coil for the nondestructive testing system of the invention.

In this embodiment, 1-loop type coils have been used in first detection coil 51 and second detection coil 52. However, when the area and the number of turns are the same, coils with a plural number of turns can also be used. FIG. 4 shows another embodiment wherein detection coil 5 is composed of 2 detection coils. That is, first detection coil 51 and second detection coil 52, whose area is equal, are aligned on the same plane, one end of first detection coil 51, one end of second detection coil 52, and one end of SQUID 4 are connected, the other end of first detection coil 51, the other end of second detection coil and the other end of SQUID 4 are connected, the direction of the current to be generated when first detection coil 51 and second detection coil 52 are positioned inside the uniform magnetic field becomes equal, and said current flows inside the closed circuit to be established by first detection coil 51 and second detection coil 52. With this configuration, when the value of the magnetic field which intersects each detection coil is the same, said current does not flow through SQUID 4 and no signal is detected. However, when the value of the magnetic field differs, the current that is in proportion to the differential amount of the magnetic field which intersects each detection coil flows through SQUID 4. Said current is transmitted to SQUID 4 and becomes the detection signal which corresponds to the differential amount of the magnetic field, and said signal is output to the processor.

Figure 5:
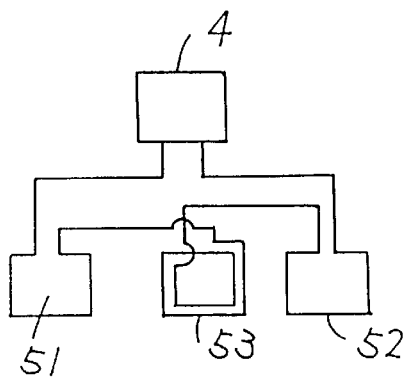
FIG. 5 is an explanation chart of the detection coil for the nondestructive testing system of the invention.

In this embodiment, 1-loop type coils have been used in first detection coil 51 and second detection coil 52. However, when the area and the number of turns are the same, coils of a plural number of turns can also be used. FIG. 5 shows an embodiment wherein detection coil 5 is composed of 3 detection coils. That is, first detection coil 51, second detection coil 52, whose area is equal, and detection coil 53, whose area is the same as that of said two detection coils, but whose number of turns are twice as many as that of said two detection coils, are aligned on the same plane, one end of first detection coil 51 and one end of third detection coil 53 are connected, the other end of third detection coil 53 and one end of second detection coil 52 are connected, the other end of first coil 51 and one end of SQUID 4 are connected, the other end of second detection coil 52 and the other end of SQUID 4 are connected, and the direction of the current to be generated when first detection coil 51, second detection coil 52, and third detection coil 53 are positioned inside the uniform magnetic filed is the same direction relative to SQUID 4 for first detection coil 51 and second detection coil 52, and is the opposite direction relative to SQUID 4 for third detection coil 53. By establishing this configuration, said current offset, as described above is not generated, and no signal is detected when the value of the magnetic field which intersects each detection coil is the same. However, when the value of the magnetic field differs, the current that is in proportion to the difference between differential amounts of the magnetic field, which intersects first detection coil 51 and third detection coil 53, and the differential amount of the magnetic field which intersects second detection coil 52 and third detection coil 53, namely, second derivative value in the uniaxial direction of the spatial magnetic distribution is generated. Said current is transmitted to SQUID 4 and becomes a detection signal which corresponds to the second derivative value of magnetic field, then said signal is output.

In this embodiment, 1-type turn coils have been used in first detection coil 51 and second detection coil 52, and 2-turn type coils have been used in third detection coil 53. However, when the volume of the area and the number of turns of the first detection coil 51 and the second detection coil 52 are the same, and the volume of the area and the number of turns of the third detection coil 53 are twice as many as those of said two coils 51 and 52, coils of a plural number of turns can also be used.

Figure 6:
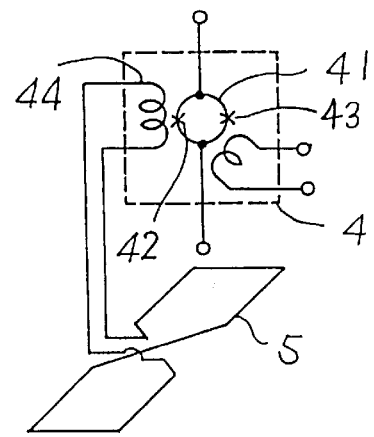
FIG. 6 is an explanation chart of the detection coil for the nondestructive testing system of the invention.

FIG. 6 shows an embodiment, wherein detection coil 5 is magnetically connected to SQUID 4. SQUID 4 is configured by a superconductive closed circuit 41 having two Josephson junctions 42 and 43, an input coil 44 and a feedback coil 45 connected thereto. Detection coil 5 in accordance with the present invention is connected to input coil 44, and thereby the detected signal is transmitted to SQUID 4.

Figure 7:
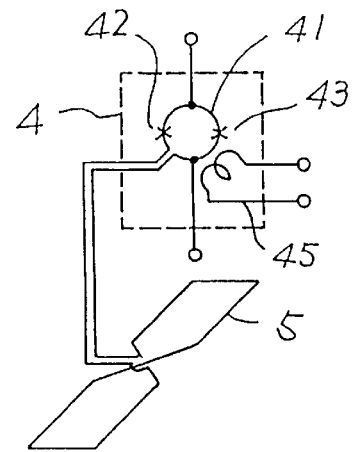
FIG. 7 is an explanation chart of the detection coil for the nondestructive testing system of the invention.

FIG. 7 shows an embodiment, wherein detection coil 5 is directly connected to SQUID 4. SQUID 4 is configured by a superconductive closed circuit 41 having Josephson junctions 42 and 43, and a feedback coil 45 connected thereto, and a detection coil 5 in accordance with the present invention is connected directly to said superconductive closed circuit 41 so that detection coil 5 forms a part of superconductive closed circuit 41. The signal detected by detection coil 5 is directly transmitted to a superconductive closed circuit 41 in a form of current signal, and thereby detected by SQUID 4.

Figure 8:
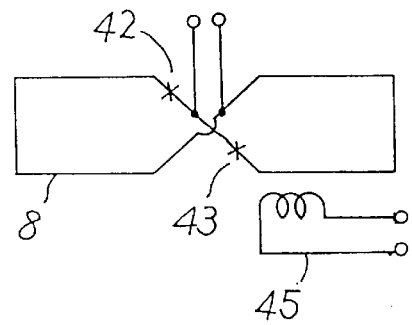
FIG. 8 is an explanation chart of the SQUID for the nondestructive testing system of the invention.

FIG. 8 shows an embodiment, wherein first detection coil 51 and second detection coil 52 are connected to SQUID 4 and both are integrated on a semiconductor substrate. In this embodiment, in order to further increase the signal transmission efficiency between detection coil 5 and superconductive closed circuit 41 in the embodiment illustrated in FIG. 7, detection coil 5, which has so far been connected to SQUID 4, and superconductive closed circuit 41, are united, integrated to form a superconductive loop having two Josephson junctions 42 and 43. Superconductive loops 8 consisting of two loops with the same area are configured on the same plane. Said two loops are symmetrical and opposite as if the one end were twisted 180° (like 8-shaped), wherein one end of said loop 8 is secured. When said superconductive loop 8 is positioned inside the uniform magnetic field, magnetic flux intersects in such a direction that individual opposite current generates in two loops. Because of this, there is no magnetic flux which actually intersects the whole loop, and, accordingly, no signal is detected. However, since the different amount of magnetic flux intersects two loops when said superconductive loop 8 is positioned inside the gradient magnetic field, for instance, the magnetic flux corresponding to the difference intersects (on) the whole of the loops, and the signal in proportion to the spatial difference of the gradient magnetic field in the distance between two loops is detected.

Figure 9:
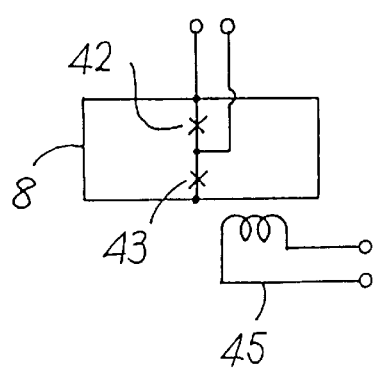
FIG. 9 is an explanation chart of the SQUID for the nondestructive testing system of the invention.

FIG. 9 shows another embodiment, wherein first detection coil 51 and second detection coil 52 are connected to SQUID 4, and they are integrated on a semiconductor substrate. This is another embodiment, wherein the shape of superconductive loop 8 is different from that illustrated in FIG. 8. However, the effect is the same. In this embodiment, said superconductive loop 8 is configured by two superconductive loops having the same area. Said loops are configured symmetrically and on the same plane, interposing two Josephson junctions 42 and 43 which are aligned in series.

Figure 10:
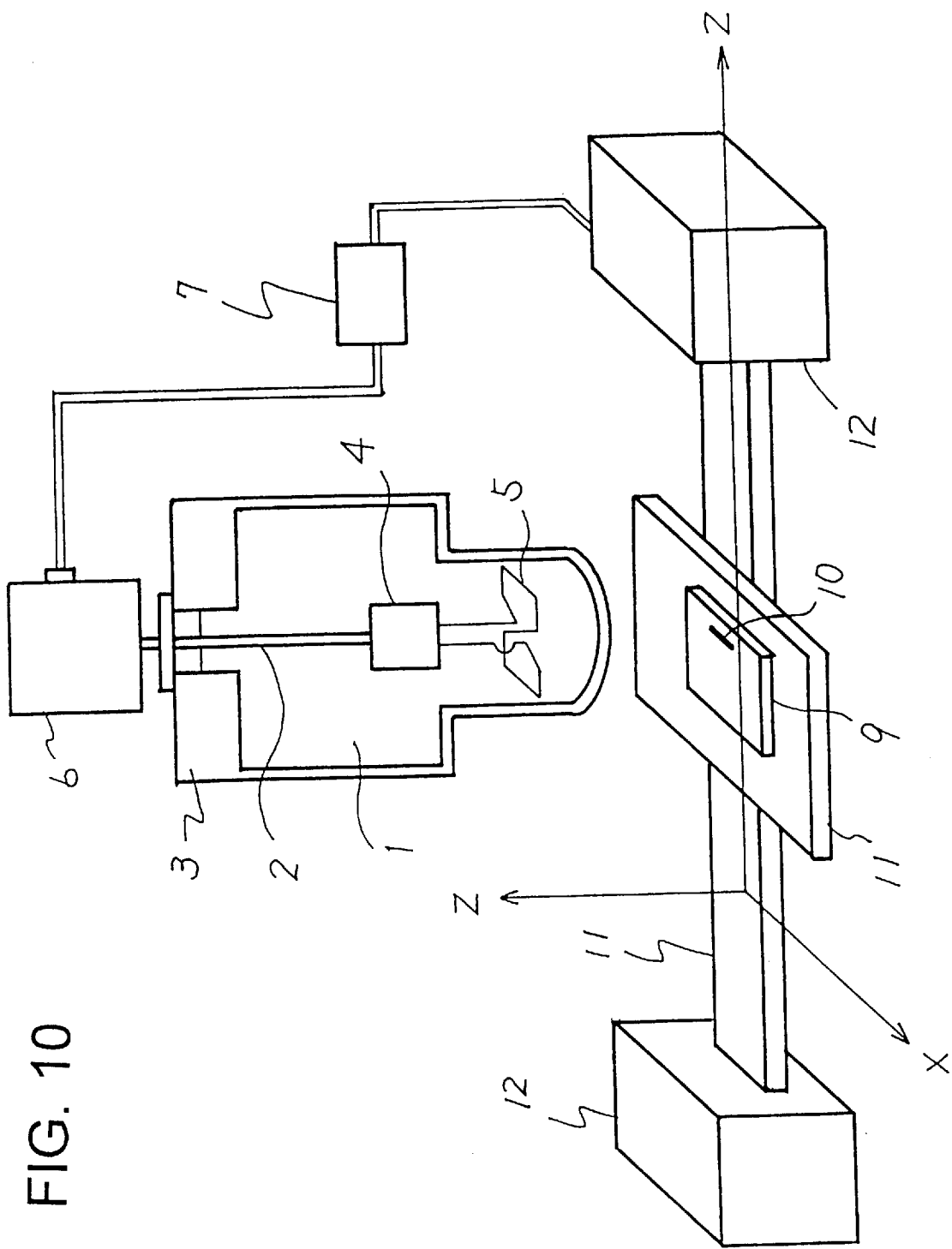
FIG. 10 shows a configuration of the nondestructive testing system of the invention.

FIG. 10 is a configuration showing an example of a nondestructive testing system in accordance with the present invention. The present invention comprises coolant 1 which produces a superconductive status, cryostat 3 which maintains said coolant and supports a probe 2, SQUID 4 attached to said probe 2, a detection coil 5, a driver 6 which is electrically connected to SQUID 4, drives SQUID 4, and measures the signal output, a movable stage 11 used for sample scanning, a stage controller 12 which drives said movable stage 11 and detects its position, a sample 9 having a scratch 10 which is placed on said movable stage 11, and signal processor which analyzes and displays the output signal from said driver 6 and the signal output from said stage controller 12.

Figure 11:
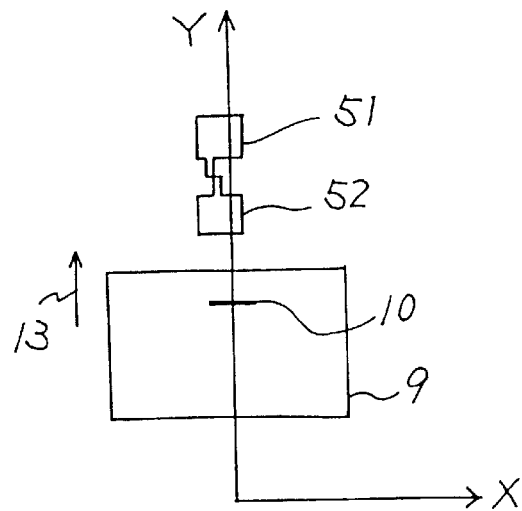
FIG. 11 is a drawing showing nondestructive testing using the nondestructive testing system of the invention.

FIG. 11 is an overview showing the positional relationship between detection coil 51 and sample 10 illustrated in FIG. 10. Detection coil 5 is the coil illustrated in FIG. 3 and is aligned so that the face to be created by first detection coil 51 and second detection coil 52 and the surface of sample 9 are parallel.

Figure 12:
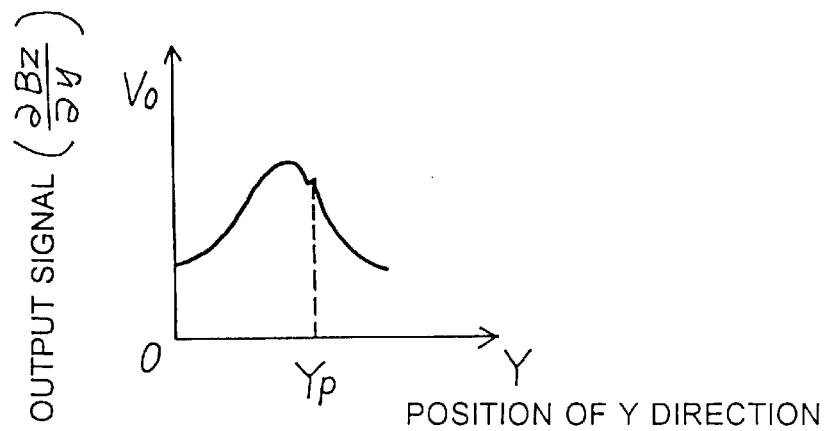
FIG. 12 shows a measurement result using conventional nondestructive testing system of the invention.

FIG. 12 is an example of measurement results obtained using conventional uniaxial embodiment according to sample scanning direction 13 illustrated in FIG.11.

Figure 2:
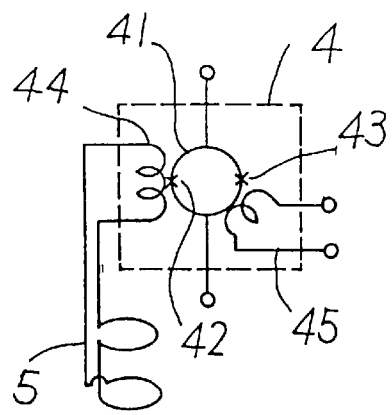
FIG. 2 shows a configuration of the conventional nondestructive testing system.
Figure 13:
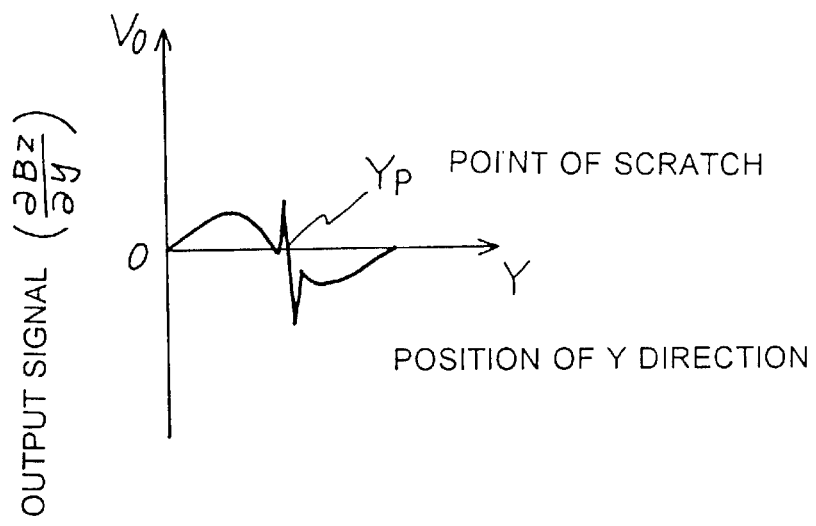
FIG. 13 shows a measurement result using the nondestructive testing system of the present invention.

FIG. 13 is an example of measurement results obtained using the present uniaxial embodiment according to said sample scanning direction 13 illustrated in FIG. 11. Change in the magnetic field due to scratch 10 is minute and significantly smaller than that of magnetic field which said sample 9 itself possesses inherently. FIG. 12 is the result obtained by measuring said sample using a conventional instrument that detects the amount of the magnetic field in the Z direction and is provided with coils illustrated in FIG. 2. In this case, substantial signal to be generated from scratch 10 is buried in background noise generated from sample 9. This makes it difficult to correctly measure the position and dimensions of the scratch. However, when measuring said sample 9 using the instrument illustrated in FIGS. 10 and 11, the result is obtained as shown in FIG. 13. Since the change in the magnetic field due to scratch 10 is significantly sharp, compared to that due to sample 9, when the change in the magnetic field is detected, a signal corresponding to the change in the magnetic field due to scratch 10 is detected by the signal lager than that corresponding to the change in the magnetic field due to sample 9. 2-dimensional nondestructive testing is also possible by using a means which activates cryostat 3 and the XY movable stage, in addition to the uniaxial movable stage illustrated in FIG. 10. Of course, either the sample stage or the probe can be scanned.

Square-type (or Squared) detection coils have been used in the present embodiment. However, the same effect is also obtained by using either round or polygonal coils. With respect to SQUID 4, the same effect can be obtained by using the RF-SQUID which is configured by the superconductive closed circuit including only one Josephson junction.

As described thus far, the following effects are obtained in accordance with the present invention;

Noise Restriction Effect: Small, weak signals buried by background noise can be detected. In the present invention, in order to detect not the dimensions, but the amount of change with respect to the magnetic field, small signals due to smaller changes in the magnetic field and large signals due to larger changes in the magnetic field can be detected. By this, background noise due to the magnetism of the Earth for which change is slow, and the inherent magnetic field that the sample itself possesses are restricted to a minimum, and signals, whose change is sharp and prompt, due to scratches, defects and change in composition are detected with high accuracy.

A Decrease in Offset Noise and an Increase in Detection Sensitivity: When a current or a magnetic field is applied externally to the sample, or measurements are done outside the magnetic shield room, offset noise can be decreased and detection sensitivity can be increased.

Improvement of Spatial Resolution: The spatial resolution for detecting micro scratches or defects to be generated in a narrow range of change in the magnetic field has been improved. Submicron-order defects can be detected using a 5 mm-square chip, onto which a 50 $\mu$m-square detection coil and SQUID are integrated on a semiconductor substrate.

Defects such as scratches which exist in a deep position away from the surface of the substance being tested can be measured.

What is claimed is:

1. A nondestructive testing unit comprising: a plurality of detection coils for detecting a magnetic field; a SQUID having a pair of Josephson junctions directly connected to the detection coils to form a closed-loop circuit consisting of the detection coils and the Josephson junctions; a probe for supporting the detection coils and the SQUID in a coolant; a cryostat for supporting the probe and keeping the coolant constant; a controller for processing a signal transmitted from the SQUID; and a display device for displaying the processing result; wherein at least two detection coils are connected with each other such that equal and opposite currents are output from the detection coils and are canceled when the detection coils are disposed in a uniform magnetic field, and the respective detection coils are disposed in the same plane.

2. A nondestructive testing unit comprising: a plurality of detection coils for detecting a magnetic field; a SQUID having a pair of Josephson junctions and a pair of connectors directly connected to the Josephson junctions and the detection coils to form a closed-loop circuit consisting of the detection coils and the Josephson junctions; a probe for supporting the detection coils and the SQUID in a coolant; a cryostat for supporting the probe and keeping the coolant constant; a controller for processing the signal transmitted from the SQUID; and a display device for displaying the processing result; wherein a first detection coil having first and second ends and a second detection coil having first and second ends are disposed in the same plane and are connected such that current flows therethrough in opposite directions, one connector of the SQUID being connected to the first end of the first detection coil, the second end of the first detection coil being connected to the first end of the second detection coil, and the second end of the second detection coil being connected to the other connector of the SQUID.

3. A nondestructive testing unit comprising: a plurality of detection coils; a SQUID having a pair of Josephson junctions and a pair of connectors directly connected to the Josephson junctions and the detection coils to form a closed-loop circuit consisting of the detection coils and the Josephson junctions; a probe for supporting the detection coils and the SQUID in a coolant; a controller for processing a signal transmitted from the SQUID; a display device for displaying the processing result; wherein a first detection coil having first and second ends and a second detection coil having first and second ends are disposed in the same plane and the first and second detection coils are looped in opposite directions, the first end of the first detection coil and the first end of the second detection coil are directly connected to one of the connectors on the SQUID, and the second end of the first detection coil and the second end of the second detection coil are directly connected to the other connector on the SQUID.

4. A nondestructive testing unit comprising: a plurality of detection coils; a SQUID having a pair of connectors for connection to the detection coils; a probe for supporting the detection coils and the SQUID in a coolant; a cryostat for supporting the probe and keeping the coolant constant; a controller for processing a signal transmitted from the SQUID; a display device for displaying the processing result; wherein a first detection coil having first and second ends and a second detection coil having first and second ends are disposed in the same plane are looped in opposite directions; a third detection coil having first and second ends aligned in the same plane as the first detection coil and looped in an opposite direction; means for connecting one of the connectors of the SQUID to the first end of the first detection coil; means for connecting the second end of the first detection coil to the first end of the second detection coil; means for connecting the second end of the second detection coil and the first end of the third detection coil; and means for connecting the second end of the third detection coil to the other connecter of the SQUID.

5. A nondestructive testing unit comprising: a plurality of detection coils: a SQUID having a pair of Josephson junctions and a pair of connectors directly connected to the detection coils and the Josephson junctions to form a closed-loop circuit consisting of the detection coils and the Josephson junctions; a probe for supporting the detection coils and the SQUID in a coolant; a cryostat for supporting the probe and keeping the coolant constant; a controller for processing a signal transmitted from the SQUID; and a display device for displaying the processing result; and wherein at least two detection coils are disposed in the same plane and are integrated on a single semiconductor substrate.

6. A nondestructive testing unit comprising: a plurality of detection coils for detecting a magnetic field; a SQUID having a pair of Josephson junctions and a pair of connectors directly connected to the detection coils and the Josephson junctions to form a closed-loop circuit consisting of the detection coils and the Josephson junctions; a processor for processing a signal transmitted from the SQUID; and a display device for displaying the processing result; wherein a first detection coil having first and second ends and a second detection coil having first and second ends are disposed in the same plane and are looped in opposite directions, one connector of the SQUID is connected to the first end of the first detection coil, the second end of the first detection coil is connected to the first end of the second detection coil, and the second end of the second detection coil is connected to the other connector of the SQUID.

7. A nondestructive testing system comprising: a SQUID having a pair of Josephson junctions; a plurality of detection coils directly connected to the Josephson junctions to form a closed-loop circuit consisting of the detection coils and the Josephson junctions, the detection coils being disposed in the same plane for detecting a magnetic field; and a processor for processing a signal transmitted from the magnetic sensor.

8. A nondestructive testing system according to claim 7; wherein the detection coils each have a first end and a second end, one end of each of the detection coils is connected to the SQUID and the other ends of the detection coils are connected to each other.

9. A nondestructive testing system according to claim 7; wherein the detection coils are connected such that a current generated by each detection coil is equal and opposite to that generated by the other when the detection coils are disposed in a uniform magnetic field.

10. A nondestructive testing system according to claim 7; wherein the SQUID and detection coils are commonly integrated on a single semiconductor substrate.

11. A nondestructive testing unit according to claim 7; further comprising a third detection coil disposed in the same plane as the pair of detection coils.

12. A nondestructive testing unit according to claim 2; wherein the first and second detection coils comprise loops of equal dimensions such that equal and opposite currents are induced in the detection coils by a uniform magnetic field.

13. A nondestructive testing unit according to claim 3; wherein the first and second detection coils comprise loops of equal dimensions such that equal and opposite currents are induced in the detection coils by a uniform magnetic field.

14. A nondestructive testing unit according to claim 5; wherein the first and second detection coils are looped in opposite directions and have equal dimensions such that equal and opposite currents are induced in the respective detection coils in response to a uniform magnetic field.

15. A nondestructive testing system according to claim 7; wherein the first and detection coils are configured such that a current induced in the first detection coil is equal and opposite to that induced in the second detection coil when the first and second detection coils are disposed in a uniform magnetic field.

16. A nondestructive testing unit comprising: a plurality of detection coils; a SQUID having a pair of Josephson junctions and a pair of connectors directly connected to the Josephson junctions and the detection coils to form a closed-loop circuit consisting of the Josephson junctions and the detection coils; a probe for supporting the detection coils and the SQUID in a coolant; a cryostat for supporting the probe and keeping the coolant constant; a controller for processing a signal transmitted from the SQUID; a display device for displaying the processing result; wherein a first looped detection coil and a second looped detection coil are disposed in the same plane and are looped in opposite directions, the first and second detection coils having a common portion, the pair of Josephson junctions being connected at first terminals thereof to the first and second detection coils at the common portion; a first terminal connected to the common portion between the Josephson junctions; and a second terminal connected to a second end of one of the Josephson junctions within the common portion.

* * * * *